US005454020A

United States Patent [19]
Solazzi

[11] Patent Number: 5,454,020
[45] Date of Patent: Sep. 26, 1995

[54] SAMPLE CUP ADAPTED FOR UPRIGHT HORIZONTAL AND INCLINED SAMPLE PLANE GEOMETRY SYSTEMS

[75] Inventor: Monte J. Solazzi, Jupiter, Fla.

[73] Assignee: Chemplex Industries, Inc., Tuckahoe, N.Y.

[21] Appl. No.: 274,233

[22] Filed: Jul. 13, 1994

[51] Int. Cl.$^6$ .................................................. G01N 23/10
[52] U.S. Cl. .............................. 378/45; 378/47; 378/208
[58] Field of Search ........................... 73/864.91, 864.82, 73/863, 864.84; 378/45, 47, 79, 208

[56] References Cited

U.S. PATENT DOCUMENTS

| | | | |
|---|---|---|---|
| 4,046,138 | 9/1977 | Libman et al. | 128/2 F |
| 4,575,869 | 3/1986 | Torrisi et al. | 378/47 |
| 4,587,857 | 5/1986 | Bush | 73/863 |
| 4,643,033 | 2/1987 | Solazzi | 13/864.91 |
| 4,698,210 | 10/1987 | Solazzi | 378/45 |
| 4,982,615 | 1/1991 | Sultan et al. | 73/864.51 |

*Primary Examiner*—David P. Porta
*Assistant Examiner*—Don Wong
*Attorney, Agent, or Firm*—Arthur L. Plevy

[57] ABSTRACT

A sample cup for holding a specimen to be analyzed by x-ray spectroscopy, comprises an enclosure having at least one wall and two open ends. The sample cup also includes sample support means removably attached to each of the two open ends and sample loading means located on the at least one wall for filling the sample cup with the specimen to be analyzed.

20 Claims, 6 Drawing Sheets

SAMPLE CUP ADAPTED FOR UPRIGHT HORIZONTAL AND INCLINED SAMPLE PLANE GEOMETRY SYSTEMS

FIELD OF THE INVENTION

This invention relates generally to a sample cup assembly for use in holding specimens for X-ray spectrochemical analysis and in particular, to such a sample cup assembly having means for filling the sample cup after it has been assembled.

BACKGROUND OF THE INVENTION

Sample cup assemblies for use in spectrochemical analysis are well known in the prior art and consist essentially of a cup-shaped cell having a closed bottom and an open top, an annular collar, and a snap-on ring. An example of a typical prior art cup is shown in U.S. Pat. No. 4,409,854 entitled SAMPLE CUP WITH EMPTYING MEANS FOR USE IN X-RAY SPECTROSCOPY issued on Oct. 18, 1983 to Michael C. Solazzi an assigned to the assignee herein Chemplex Industries Inc. As can be seen, the collar and the snap-on ring serve to secure a sheet of plastic material such as MYLAR, the trademark for a polyester film sold by E.I. dupont de Nemours and Co., to cover the open top of the cell when the cell is filled with a specimen to be analyzed. The surface of the sheet of plastic is commonly defined as the sample plane.

The ability to statistically reproduce the distance from the sample plane to the excitation source is of utmost importance for exacting X-ray spectrochemical analysis. Deviations which may occur in this distance from one sample presentation to another will be reflected in the degree of analytical accuracy. This is because any variations in this distance operates to alter the intensity of the characteristic radiation of the specimen and the intensity of the radiation impinging upon the sample from the excitation source. Several factors have been discovered that predominately control the sample plane to excitation source distance. These factors include the geometry of the instrumentation optics, the type of sample substance, positioning of the specimen in the instrument sample chamber, heat generation from the excitation process, and pressure differentials attributed to operating in an evacuated or positive pressure condition and sample out-gasing. Any one of these factors or any combination thereof will effect the analytical data and care must be exercised in minimizing the influence of these factors on the analysis.

Most commercially available X-ray analytical instruments are designed with inverted optics geometry. The excitation source in this arrangement is located beneath the sample and provides a sample plane which is horizontally positioned above the optics. A liquid and/or loose powdered sample substance is generally gravity supported on a thin film substance attached to the sample cup. In this arrangement, the thin film substance, as mentioned above, defines the sample plane. In order to maintain a statistically reproducible sample plane to excitation source distance, allowances must be made for thin film distortion which is attributed to thermal and pressure differences. The distortion either increases or decreases the distance between the sample plane and the excitation source which results in higher or lower values than would be had without the distortion.

The sample preparation procedure for the above described arrangement, however, is relatively simple as it consists of merely ensuring that the sample cup contains an adequate quantity of sample substance such that the required critical depth of penetration is satisfied.

Other types of instrumentation have configurations and arrangements that require an upright, horizontal, or inclined sample plane. These arrangements generally require more manual dexterity in accommodating a liquid type specimen than do the inverted geometry arrangements described earlier. This increase in manual dexterity is required in order to maintain a reproducible and uniform distance from the sample plane to the excitation source. Thus, the difficulties associated with X-ray systems of this classification are related to convenience which impacts on the ability to statistically reproduce the distance of the sample plane to the excitation source.

The initial introduction of the sample substance to the main cell of the sample cup assembly, the attachment of the thin film to the open end of the main cell and the retention of the sample within the sample cup during the analysis, generally demands a great deal of time and effort on the part of the technician because the sample plane is located at the top of the sample cup assembly. In order to define the sample plane, the sample cup assembly must be completely filled prior to attachment of the thin film substance and particularly to avoid entrapment of air. Furthermore, the thermal and pressure differentials frequently encountered result in the creations of bubble occlusions within the liquid specimen that generally rise and collect at the interface of the thin film substance and sample surface. This condition can potentially create erroneous analytical data.

In upright horizontal sample plane geometries, bubble occlusions tend to randomly disburse at the surface of the liquid specimen and beneath the thin film substance. In contrast, bubble formations which occur with instruments utilizing inclined sample plane geometries, collect and are generally confined to the upper most area of the sample cup assembly. The focal area of X-ray impingement on the sample, however, is generally small enough to allude the effects of the side collected bubble occlusions on the analytical data.

Until now, no prior art sample cup assemblies have been designed to comprehensively resolve all the difficulties associated with analyzing liquid samples in upright, horizontal, or inclined sample plane systems without having to resort to intricate and costly sample cup designs and methods that are generally very time consuming for assembly and for the most part, are not entirely effective. Moreover, prior art liquid cells primarily designed for inverted optics are also used for upright, horizontal, inclined sample plane geometry systems. The design of these sample cup assemblies allows air to remain entrapped at the interface of the liquid sample plane and the thin film sample support material. The present invention addresses the problems associated with prior art sample cup assemblies by providing a sample cup assembly having a main cell with two open ends which must be assembled. Such cups have been used in many different fields of endeavor as can be seen be looking at U.S. Pat. No. 4,046,138 DIAGNOSIS DEVICE FOR LIQUID SAMPLES issued on Sep. 6, 1977 to Gary Lipin et al., U.S. Pat. No. 4,587,857 entitled METHOD FOR MOUNTING POORLY CONSOLIDATED CORE SAMPLES issued on May 13, 1986 to Darrell C. Bush, and U.S. Pat. No. 4,982,615 entitled STERILE CONTAINER FOR COLLECTING BIOLOGICAL SAMPLES FOR PURPOSES OF ANALYSIS issued on Jan. 8, 1991 to Bernard Sultan et al. All of these patents disclose sample holders with a main cell having two open ends which must be assembled, however, none of these sample cup assemblies are designed for use in X-ray spectroscopy. Furthermore, the present invention also provides means for filling the sample cup once the parts of the sample cup assembly have been assembled. Such a feature is not disclosed or suggested in any of the prior art patents described above.

It is, therefore, an object of the present invention to provide an improved sample cup assembly which includes means for conveniently filling the sample cup once it is assembled without entrapping air at the sample liquid/sample support film interface.

SUMMARY OF THE INVENTION

A sample cup for holding a specimen to be analyzed by x-ray spectroscopy, comprises an enclosure having at least one wall and two open ends. The sample cup also includes sample support means removably attached to each of the two open ends and sample loading means located on the at least one wall for filling the sample cup with the specimen to be analyzed.

The present invention also includes a method for filling a sample cup comprising the steps of installing a thin film of material on each open end of a main cell formed by at least one wall, puncturing a hole in a diaphragm member located on the at least one wall, inserting a needle of a syringe filled with a liquid specimen to be analyzed into the hole, injecting the liquid specimen into the main cell to fill the main cell with the specimen and sealing the hole with a closure.

DETAILED DESCRIPTION OF THE INVENTION

Figure 1:
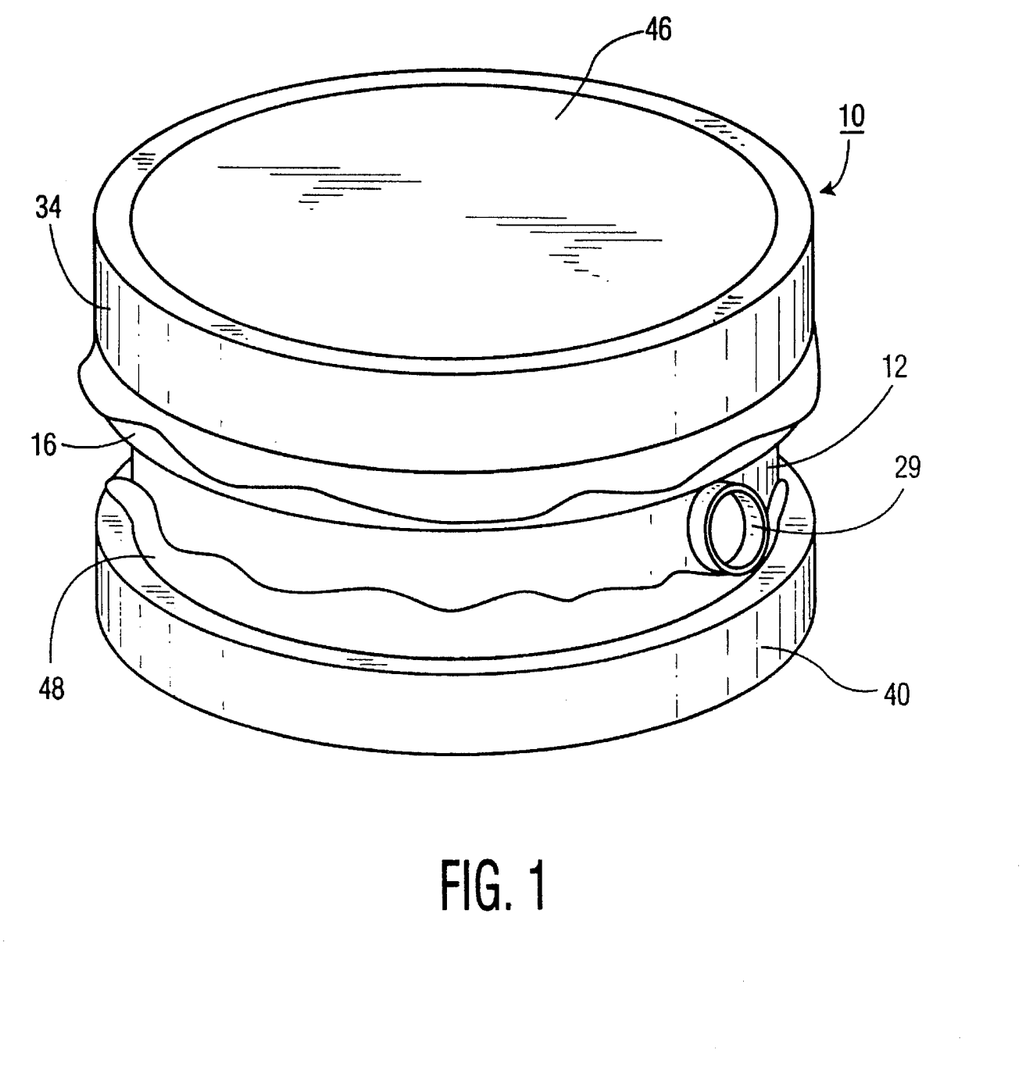
FIG. 1 is a perspective view of a sample cup according to the present invention.

Referring now to FIG. 1 there is shown an exemplary embodiment of a sample cup according to the present invention designated by the numeral 10. Generally, the sample cup 10 consists of a main cell component 12, a first collar 34 which is used in holding a first sample supporting film 46 over the open top of the main cell 12 and a second collar 40 which retains a second sample supporting film 48 over the open bottom of main cell 12. The main cell 12 is provided with a sample loading port 29 which will be described in greater detail below.

Figure 2:
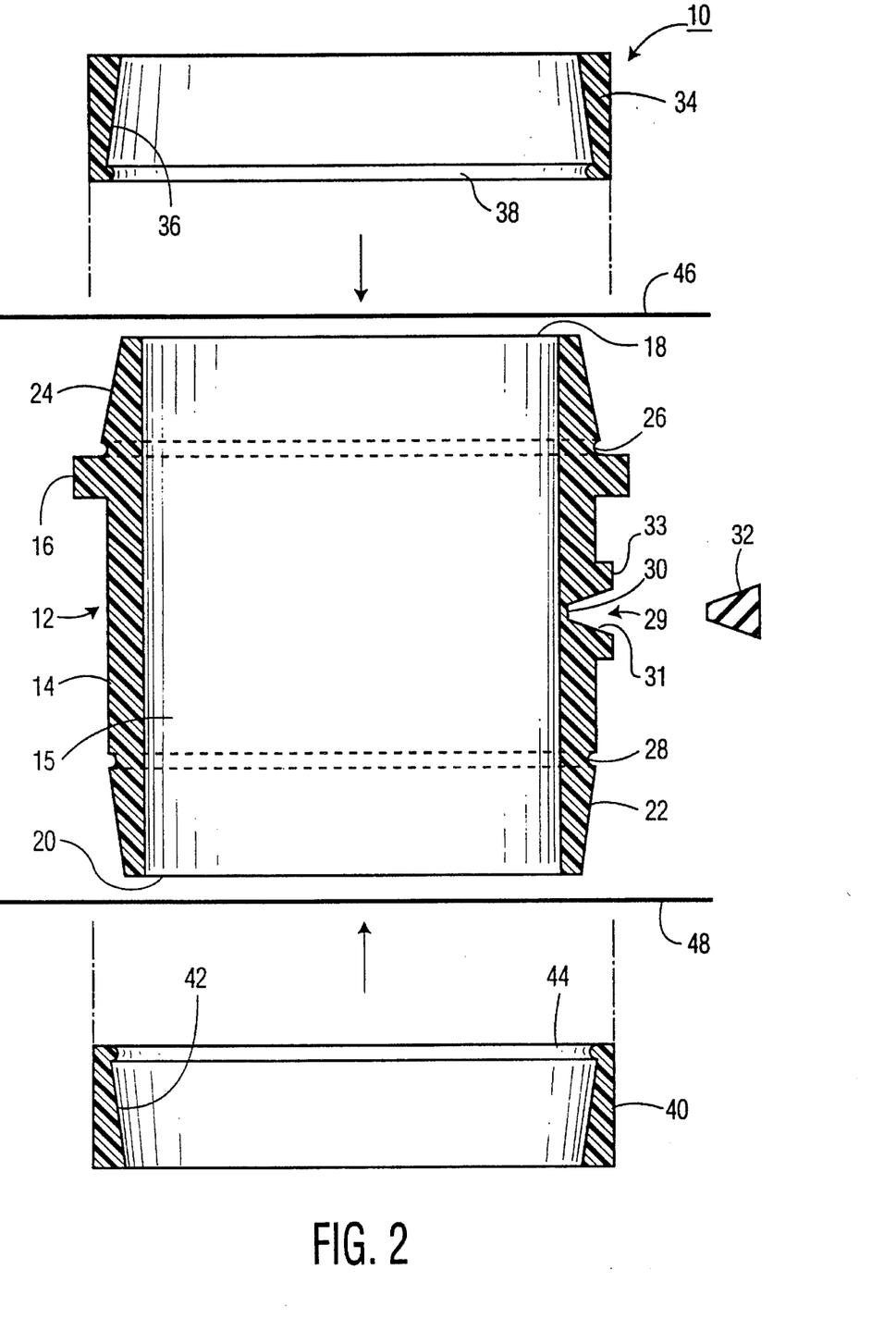
FIG. 2 is an exploded cross-sectional view of the sample cup of FIG. 1.

Referring now to FIG. 2 there is shown an exploded view of the individual components of the sample cup 10 shown in FIG. 1. As can be seen in FIG. 2, main cell 12 comprises a generally cylindrical wall 14. The outer surface of the cylindrical wall 14 presents a first tapered surface 24 at the open top 18 of the main cell 12 and a second tapered surface 22 at the open bottom 20 of main cell 12. A first circumferential groove 26 is provided at the interface of tapered surface 24 and cylindrical wall 14. Similarly, a second circumferential groove 28 is provided at the interface of tapered surface 22 and cylindrical wall 14. Each tapered surface and its associated groove coact with each other to retain their respective collar member as will be described in further detail below.

Referring still to FIG. 2, first and second collar members 34 and 40 respectively, are shaped to conform generally with the shape of the main cell 12 which in this embodiment is defined generally by cylindrical wall 14. It should be understood, however, that main cell 12 can be shaped in any suitable configuration such as square, rectangular, or oval. Accordingly, the collar members would be adapted to conform with the chosen shape of the main cell. In any event, the first and second collar members 34 and 40 have respective inner surfaces 36 and 42 which are adapted to correspond to tapered surfaces of the main cell. Collars 34 and 40 each include a respective extending circular projection or flange 38 and 44. These flanges are adapted to fit within respective grooves 26 and 28 on the main cell 12 to hold the collars in place on the cell as will be further described below.

Main cell 12 also includes a circumferential flange 16 located just below the first circumferential groove 26 on cylindrical wall 14. The circumferential flange 16 allows the sample cup 10 to be placed into a holding fixture (not shown) which can be optionally used to support the sample cup. In such applications, the circumferential flange 16 allows the sample cup 10 to be properly aligned within the holding fixture. The circumferential flange 16 also provides a place for grasping and handling the sample cup.

Figure 6:
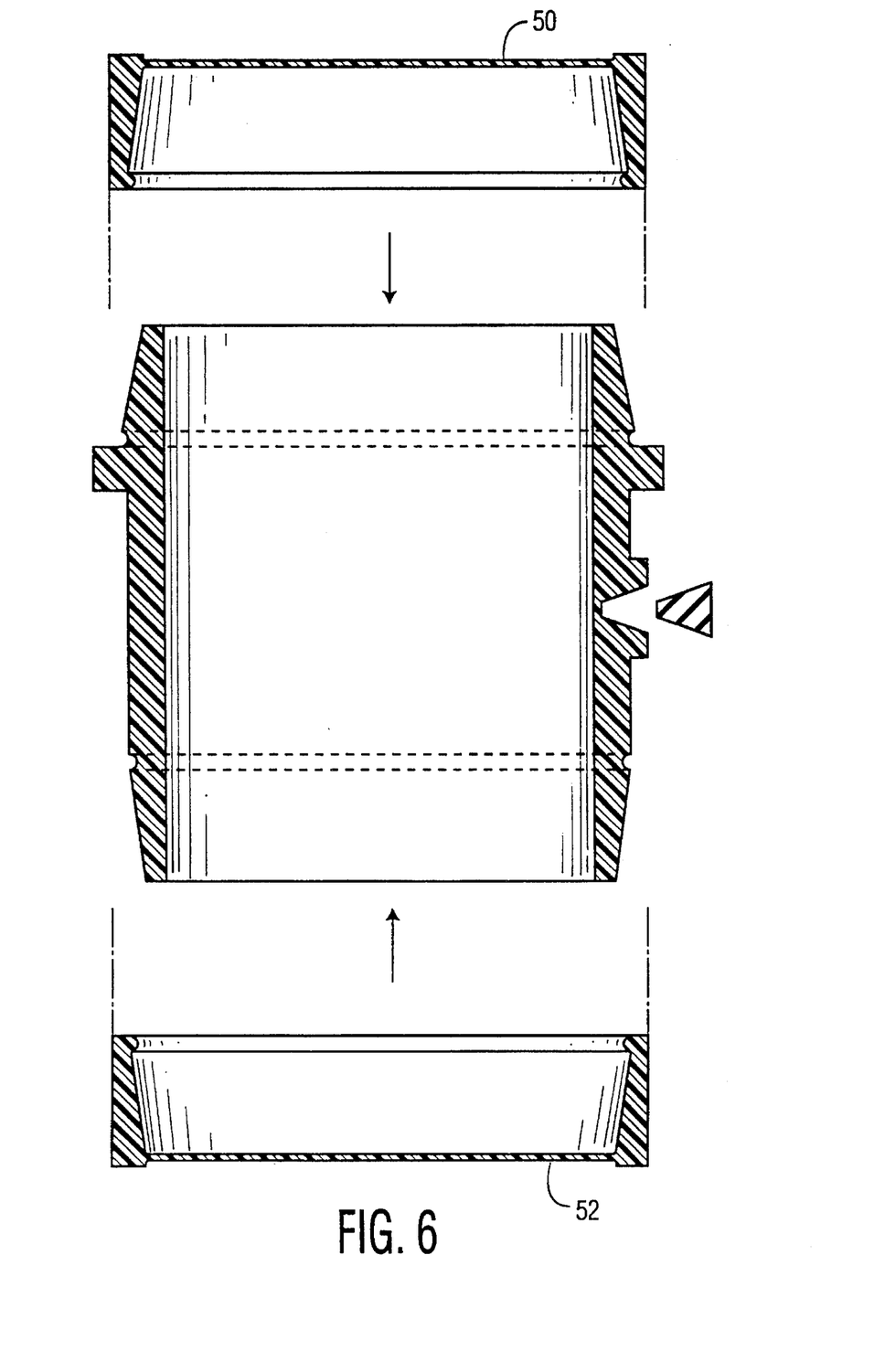
FIG. 6 is exploded partial cross-sectional view of an alternative embodiment of the present invention.

Also shown in FIG. 2 are two individual thin sample supporting films 46 and 48. These films form the top and bottom walls of the sample cup when they are assembled to the main cell 12 using collars 34 and 40. Alternatively, however, each sample supporting film can be integrally molded with the annular collar as a unitary member as shown in FIG. 6 and designated by numerals 50 and 52. Integrally molded sample supporting film/annular retaining collar arrangements are discussed in greater detail in U.S. Pat. No. 4,643,033 entitled SAMPLE CUP FOR USE IN X-RAY SPECTROSCOPY issued to Monte J. Solazzi on Feb. 17, 1987 and assigned to Chemplex Industries, Inc., the assignee herein. The portions of U.S. Pat. No. 4,643,033 dealing with this subject is incorporated herein in its entirety.

Accordingly, the sample supporting films are preferably fabricated from a polyester, polypropylene, polyethylene, or a polycarbonate material although any suitable material can be used. The main cell and the collars are preferably fabricated from any suitable plastic such as polypropylene or the like. Polypropylene and other like plastics are desirable because they offer rigidity and have resistance to chemical attack. Thus these plastics are very practical for use as sample cup structures, although any other suitable materials can be used.

As briefly mentioned above, the sample cup 10 shown in FIGS. 1 and 2, is provided with a specially designed sample loading port 29 in wall 14 of the main cell 12 which allows the sample cup to be loaded in the fully assembled state. The sample loading port 29 comprises a frustoconically shaped wall 31, a raised locating ring 33 which surrounds the sample loading port and an integrally formed diaphragm member 30 which seals the bottom of the sample loading port. The diaphragm member is integrally formed to provide the flexibility of also using the sample cup 10 for upright sample geometry systems whereby the bottom end of the main cell is first assembled, the cell then being oriented in the upright position and filled by introducing the liquid sample through the unassembled open top of the cell instead of through the sealed sample loading port 29. After filling, the main cell is then fully assembled by attaching the supporting film to the open top of the main cell.

The sample loading port 29 feature of the present invention, however, is provided to allow concurrent filling of the fully assembled cell and expulsion of any entrapped air from within the cell as most or virtually all the entrapped air is displaced by the occupation of the liquid sample. This is accomplished by introducing the liquid sample through loading port 29 using a syringe as will be explained in greater detail below.

When the sample loading port 29 is utilized in filling the main cell with a liquid sample, a generally frustoconically shaped plug 32 is provided to plug the loading port after filling is completed. Plug 32 is preferably made from an elastically deformable material such as rubber or the like. The shape and outer dimensions of the plug are adapted to allow the plug to fit snugly within the space defined by wall 31 of loading port 29 to seal the puncture in the diaphragm of the port made during filling of the cell.

Figure 3:
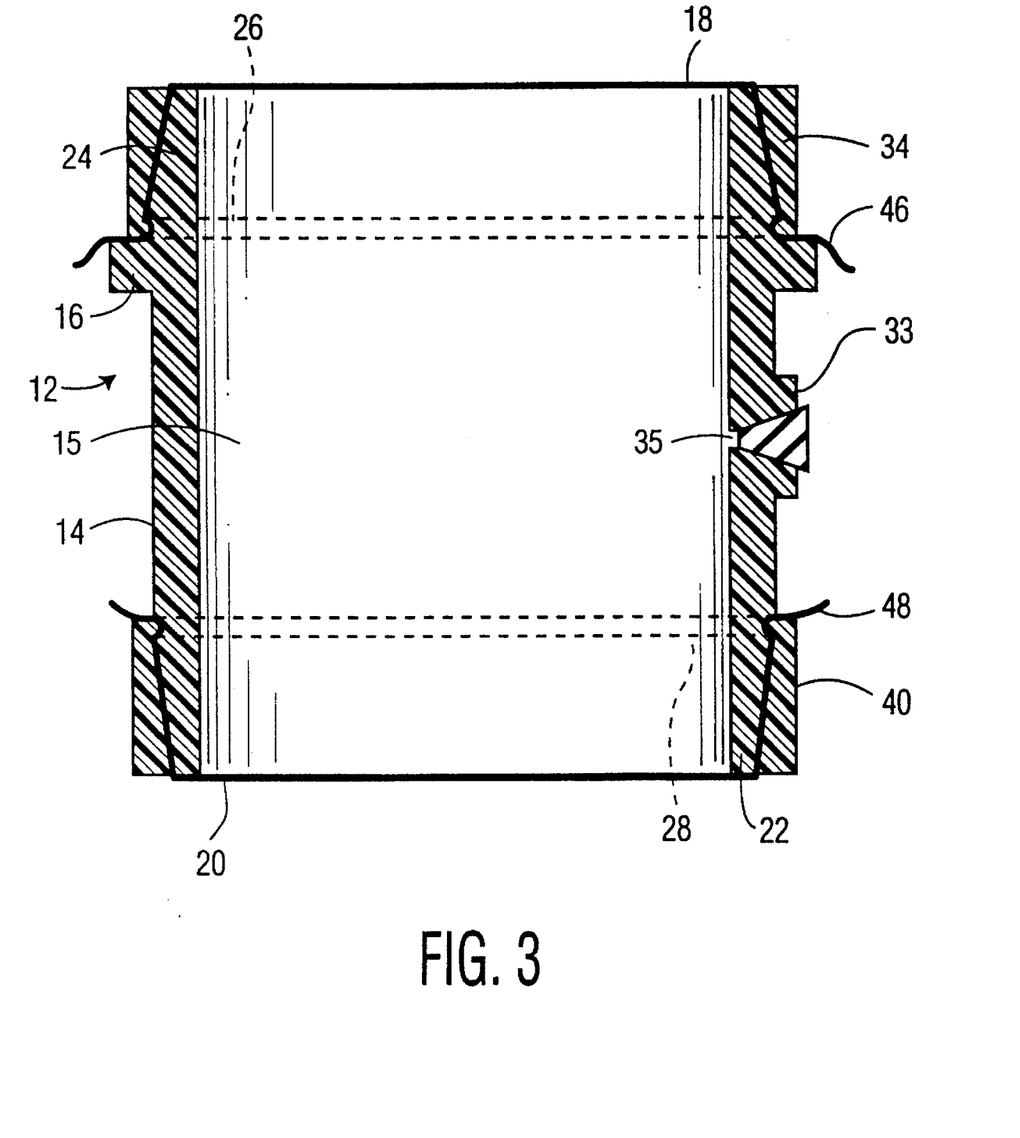
FIG. 3 is a cross-sectional view of the sample cup of FIG. 1.

Referring now to FIG. 3 there is shown a cross-sectional view of the sample cup of FIGS. 1 and 2 in the fully assembled state with a puncture 31 made in the diaphragm 30 of loading port 29 and plug 32 installed therein. As can be seen the sample supporting films 46 and 48 are each held in place over their respective open top and bottom portions of main cell 12 by collars 34 and 40 respectively. The films are each maintained in a taut and wrinkle free state by the clamping action provided between the tapered surfaces of the main cell and the inclined inner surfaces of their respective collars. Additional clamping action is provided between the grooves and the flange members of their respective collars.

Figure 4A:
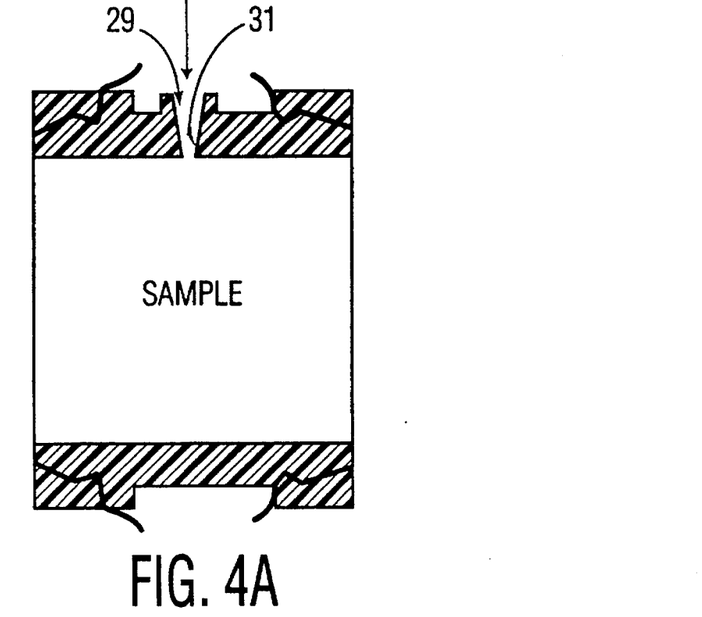
FIGS. 4A and 4B shows the operation of the sample loading port.
Figure 4B:
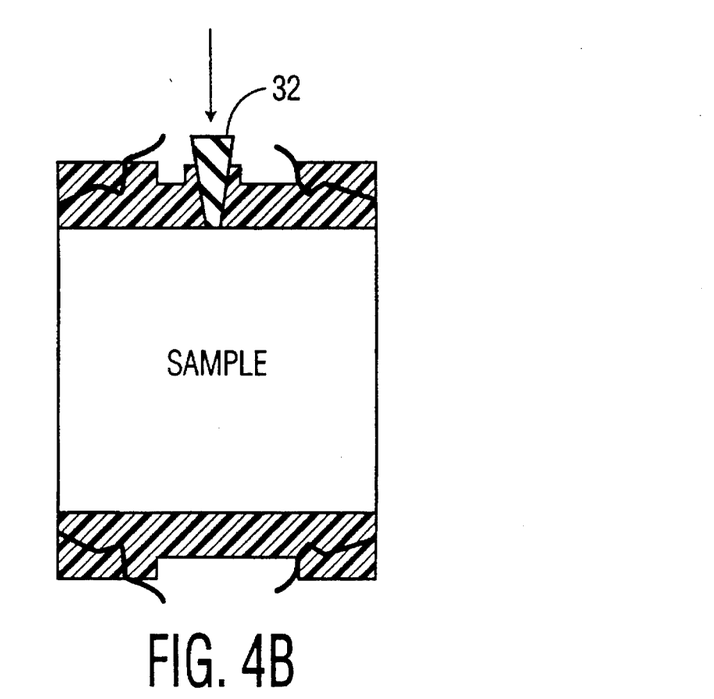

Referring now to FIGS. 4A and 4B, a method of using of the sample cup of the present invention will be described. First, the sample cup assembly of the present invention is completely assembled by affixing each of the supporting films over its respective open end of the main cell. The sample cup assembly is then oriented sideways and the sample cup is rotated so that the locating ring 33 around the sample loading port 29 is facing upward as shown in FIG. 4A. A sharp object (not shown) is used to puncture the diaphragm 30 of the sample loading port 29 such that the diameter of the puncture is slightly larger than the diameter of the syringe used for loading the sample into the sample cup assembly. Next, the syringe containing the liquid specimen to be analyzed is inserted into the puncture and the liquid specimen is injected into the main cell. The slightly larger diameter of the puncture allows entrapped air from within the cell to escape through the space provided between the puncture and the syringe as the main cell is loaded. After completion of filling and the examining for the absence of air occlusions, the cell is sealed with the friction fitting plug 32 as shown in FIG. 4B.

Figure 5A:
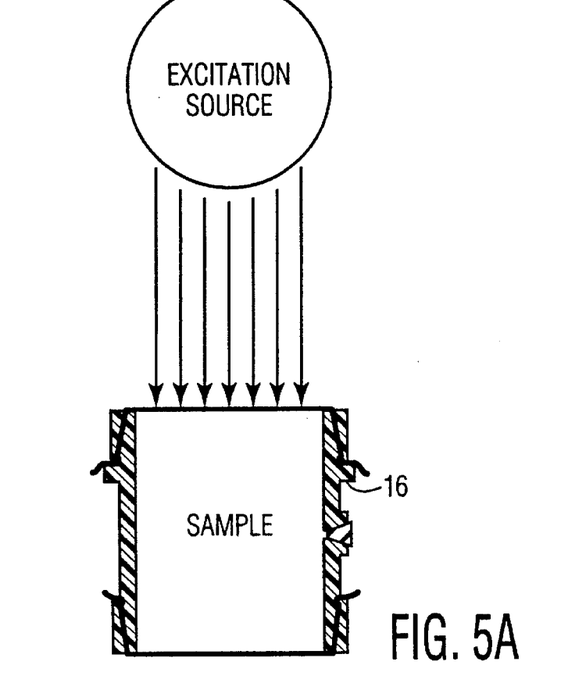
FIGS. 5A and 5B shows how the sample cup of the present invention is used in both the upright horizontal and inclined sample plane orientations.
Figure 5B:
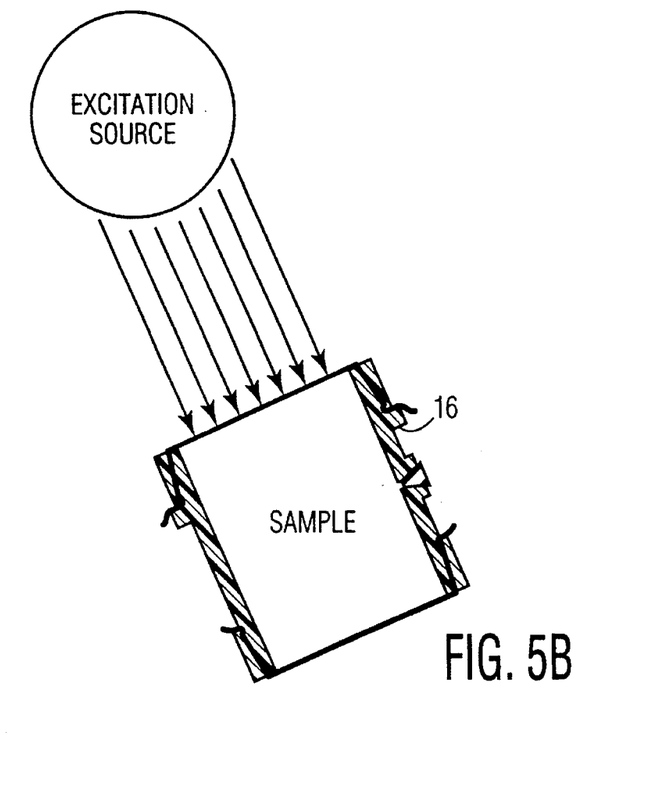

The filled sample cup assembly can now be used in either an upright horizontal sample plane position as shown in FIG. 5A or can be used in an incline sample plane as shown in FIG. 5B. In presenting the sample to the instrument for analysis, the end of the assembled sample cup assembly containing the circumferential ridge 16 must be oriented upwardly as shown in FIGS. 5A and 5B.

It should be understood that the embodiments described herein are merely exemplary and that a person skilled in the art may make many variations and modifications to the described embodiments utilizing functionally equivalent elements to those described herein. Any variations or modifications to the invention just described as well as others which may become apparent to those skilled in the art are intended to be included within the scope of the invention as defined by the amended claims.

I claim:

1. A sample cup for holding a specimen to be analyzed by x-ray spectroscopy, comprising:

an enclosure having at least one side wall extending between two open ends;

sample support means removably attached to each of said two open ends; and sample loading means located on said at least one side wall for filling said sample cup with said specimen to be analyzed.

2. The sample cup according to claim 1, further comprising detachable retaining means for removably attaching said sample support means to each of said two open ends.

3. The sample cup according to claim 1, further comprising closure means for sealing said sample loading means after said sample cup is filled with said specimen.

4. The sample cup according to claim 1, wherein said enclosure is made from plastic.

5. The sample cup according to claim 1, wherein said sample supporting means is a thin film removably attached to each of said two ends.

6. The sample cup according to claim 5, wherein said thin film is made from plastic.

7. The sample cup according to claim 2, wherein said detachable retaining means is a pair of collars each of which is adapted to clamp one of said thin films to a respective one of said two ends.

8. The sample cup according to claim 1, wherein said sample loading means comprises a thin diaphragm formed in said at least one side wall of said enclosure and adapted to be punctured by a syringe needle.

9. The sample cup according to claim 8, wherein said sample loading means further comprises locating means for locating said sample loading means.

10. In a sample cup assembly of the type used for holding a specimen to be analyzed by x-ray spectroscopy and comprising a main cell having at least one side wall extending between two open ends, a pair of thin films each of which is removably attached to a respective one of said two ends when said sample cup assembly is assembled, each of said films operating to support said specimen within said main cell, the improvement therewith comprising:

sample loading means positioned in said at least one side wall for filling said main cell with said specimen to be analyzed, after said sample cup is assembled.

11. The sample cup assembly according to claim 10, further comprising detachable retaining means for removably attaching each one of said pair of thin films to said two open ends.

12. The sample cup assembly according to claim 11, wherein said detachable retaining means is a pair of collars each of which is adapted to clamp one of said thin films to a respective one of said two ends.

13. The sample cup assembly according to claim 10, further comprising closure means for sealing said sample loading means after said sample cup is filled with said specimen.

14. The sample cup assembly according to claim 10, wherein said sample loading means comprises a pierceable member formed in said at least one wall of said cell.

15. The sample cup assembly according to claim 14, wherein said sample loading means further comprises locating means for locating said sample loading means.

16. A method for filling a sample cup used in an upright horizontal and inclined sample plane systems employed in x-ray spectrochemical analysis, comprising a main cell formed by at least one side wall extending between two open ends, said method comprising the steps of:

installing a thin film of material on each open end of said main cell;

puncturing a hole in a diaphragm member located on said at least one side wall;

inserting a needle of a syringe filled with a liquid specimen to be analyzed into said hole;

injecting said liquid specimen into said main cell to fill said main cell with said specimen; and sealing said hole with a closure.

17. The method according to claim 16, wherein said step of installing includes sliding a retaining collar over each of said thin films to secure said thin films to said main cell.

18. The method according to claim 16, wherein said hole made during said step of puncturing is of a diameter which is slightly greater than the diameter of said needle of said syringe to provide a space for the expulsion of air entrapped within said cell during filling of said cell with said specimen.

19. The method according to claim 16, wherein said main cell includes a circumferential ridge which is located closer to one of said two open ends and further comprising the step of:

placing said sample cup in an upright horizontal sample plane x-ray spectrochemical analysis system and orienting said sample cup so that said circumferential ridge is oriented upwardly.

20. The method according to claim 16, wherein said main cell includes a circumferential ridge which is located closer to one of said two open ends and further comprising the step of:

placing said sample cup in an inclined sample plane x-ray spectrochemical analysis system and orienting said sample cup so that said circumferential ridge is oriented upwardly.

* * * * *